United States Patent [19]

Heinz

[11] 4,347,734
[45] Sep. 7, 1982

[54] ROTARY VISCOMETER

[76] Inventor: Werner Heinz, Dabringhauser Strasse 72, Koeln, Fed. Rep. of Germany

[21] Appl. No.: 162,945

[22] Filed: Jun. 25, 1980

[30] Foreign Application Priority Data

Jun. 27, 1979 [DE] Fed. Rep. of Germany ....... 2925904

[51] Int. Cl.³ .......................................... G01N 11/14
[52] U.S. Cl. ...................................................... 73/59
[58] Field of Search ..................................... 73/59, 60

[56] References Cited

U.S. PATENT DOCUMENTS

| | | | |
|---|---|---|---|
| 2,679,750 | 6/1954 | Brookfield | 73/59 |
| 2,703,006 | 3/1955 | Savins | 73/59 |
| 3,435,666 | 4/1969 | Fann | 73/59 X |
| 3,886,789 | 6/1975 | Brookfield | 73/59 |
| 3,935,726 | 2/1976 | Heinz | 73/60 |

FOREIGN PATENT DOCUMENTS 14934 4/1953 Fed. Rep. of Germany .......... 73/59

Primary Examiner—Stuart S. Levy
Assistant Examiner—Joseph W. Roskos
Attorney, Agent, or Firm—Colton & Stone, Inc.

[57] ABSTRACT

In a rotary viscometer comprising a variable speed drive motor including a speed indicator, such as a tachogenerator or a similar device, and a measuring shaft driven by an output shaft of a rotor of said motor and carrying a measuring member immersible in a medium of which the viscosity is to be measured, the motor stator is rotatably displaceable against the action of a spring, the displacement being a measure of the viscosity. The driving connection between said motor and measuring shaft comprises at least one pair of exchangeable gears or toothed belts and said spring is exchangeable for one having a different spring characteristic.

14 Claims, 4 Drawing Figures

ROTARY VISCOMETER

The invention relates to a rotary viscometer comprising a variable speed electric drive motor including a speed indicator, such as a tachogenerator or a similar device, a measuring shaft driven by said motor, and a measuring member at one end of said measuring shaft for immersion in a medium to be measured, the stator of said motor being rotatably mounted on a base block by means of a support and subjected to the return force of a spring, the rotary deflection of said stator from a rest position being measurable over a short path.

Rotary viscometers are known in which a synchronous gear motor or a regulated D.C. motor drives a measuring member which is immersed in the substance to be tested. The motor is accommodated in a rotatably mounted support. The torque exerted on the measuring member during measurement results in a counter-torque (reaction torque) which acts on the support and corresponds to the viscosity. As a result of this counter-torque, the support executes rotary movement against the force of a spring. The small distance that is traversed thereby is measured by an electric transducer over a short path.

To enable statements to be made about the rheological behaviour and for the purpose of adapting to very different viscosities, it is desirable that equipment of this kind should permit very large rotary speed ranges to be covered and this, in turn, gives rise to a large range of the resulting torques.

Embodiments are therefore known for such rotary viscometers, in which gearing between the motor and measuring member was in the form of multi-stage change gearing, the gears being changed manually or by means of electromagnets.

Other known embodiments comprise change gearing with step-down ratios depending on the direction of rotation of the motor.

In these known embodiments, the gearing is complicated to produce and heavy in weight, which results in higher manufacturing costs and increased friction at the bearings.

The different ranges of torque resulting from very different rotary speeds in the case of the known embodiments are detected by switching over the transducer electrically. However, by reason of the limits of error of the electric transducer, the possible range is restricted.

Viscometers having a mechanical pointer display are known, in which a plurality of measuring springs of different characteristics are provided in series or in parallel and are brought into operation depending on the desired measuring range. In such equipment, there are large spring displacements but large spring displacments can detrimentally influence the measuring accuracy of the electric transducer because the latter must operate linearly over a considerable range.

The difficulties are therefore that, on the drive side, a large rotary speed range must be provided, with the cost and friction being kept small, and that on the measuring side one must provide a wide range in which a torque can be accurately measured. Measurement over a short path should be aimed at because of the inherent accuracy. The previously mentioned arrangement in which a plurality of measuring springs are disposed in series or in parallel does not make this possible.

It is therefore an object of the present invention to provide a rotary viscometer which has a wide range of rotary speed but can nevertheless accurately measure despite this large range of rotary speed. The invention is based on the consideration that modern electronics permit the control range of an electrically controlled D.C. motor as well as the measuring range of an electric distance or angle transducer to be very large so that adaptation of the equipment to the measuring problem need only occasionally go beyond the purely electric possibilities.

According to the invention, the force path or operative connection between the motor and measuring shaft includes at least one pair of exchangeable gears or toothed belts, and one of a plurality of springs having different characteristics is selectively insertable between the motor support and the base block. Thus, if the range of rotary speed achievable by a regulated motor is insufficient, manual replacement is effected of two gears or a pair of toothed belts between the motor and measuring shaft to provide a different transmission ratio. At the same time, if a different torque range is also produced, the spring on the measuring side is replaced by one having a different characteristic. The principle of accurate measurement over a short path is maintained. The gears or belts and springs are manually exchanged.

A large torque range calls for a low amount of friction. For this purpose, the support is preferably part of a hollow shaft and the measuring shaft extends through and is mounted in said hollow shaft. The hollow shaft can be mounted in bearings having a small internal and external diameter and thus giving rise to little friction.

To facilitate the exchangeability of the gears or belts, the axes of the motor and hollow shaft may be parallel. This is achieved by appropriate arrangement of the motor on its support.

Desirably, the hollow shaft passes through the base block and is mounted therein, the motor and spring being disposed above the base block. The exchangeable gears or belts with which the rotary speed ranges are set as well as the exchangeable springs with which the different torque ranges to be measured are covered will then be easily accessible. The user can manipulate them easily and exchange them without being substantially hindered by parts of the equipment.

In a further desirable embodiment, the output shaft of the motor is disposed at the top and the pair of gears or toothed belts is disposed between the output shaft and the parallel upper end of the measuring shaft. The gears or belts to be exchanged are therefore disposed at the very top of the equipment and are particularly simple to exchange. The gears or belts are simply placed on the free upper ends of the output and measuring shafts. The motor and measuring shafts are juxtaposed.

To increase the measuring accuracy still further, the blind friction is reduced which occurs at the bearing of the hollow shaft from taking up the weight of the motor, its support, the gears, a counterweight etc. More particularly, annular permanent magnets which repel each other can be coaxially disposed on the base block and hollow shaft coaxial with the hollow shaft. These magnets take up the weight of the aforementioned components either entirely or partially. This relieves the bearings for the hollow shaft. This relief is particularly important for low rotary speeds and thus low torques if weak springs are being used to measure the torque. The invention will then provide a high accuracy particularly in this lower measuring range. Desirably, one permanent magnet has a smaller external and a larger internal diameter than the other. If the two magnets cannot be precisely superposed because of tolerances during their manufacture, any side components of the repelling force are kept small with the aid of these diameters.

The hollow shaft is mounted in the base block. According to one aspect of the invention, the part of the hollow shaft disposed within the base block comprises at least one section of enlarged diameter and a first bearing for the measuring shaft is inserted in said section, second bearings for mounting the hollow shaft in the base block having the same external diameter as the first bearing. This provides the advantage of making it possible to use small bearings and bearings having the same external diameter.

The springs are preferably helical and carry sleeve or clip-like terminals. These terminals, by which the springs are placed on supports, are welded, soldered or cemented to the springs. One terminal of the spring or one support is disposed on the base block whereas the other terminal of the spring is supported against the stator of the motor or its support or the hollow shaft. In practice, this terminal of the spring is connected to an arm seated on the hollow shaft.

For measurement over a short path, it is important for the spring to assume exactly the same position relatively to the support and relatively to the fixing device after it has been exchanged. This is true for all six possible degrees of movement of the spring, i.e. including any possible rotation of the spring about its longitudinal axis. For the very small measuring distances by which the spring is displaced and the consequent high stiffness of the spring, the position of the mounted spring terminals has a large influence on the spring characteristic. In the present invention, therefore, the sleeve or clip-like terminals and the supports therefor are preferably constructed so that the springs are insertable in only one defined position. This can, for example, be done if the sleeve or clip-like terminals are flattened at the top and it is only this flat shape with which they can co-operate with a clamping plate to be placed thereon. Another way is to make the sleeve or clip-like terminals at the ends of the springs of different length. One end will fit only on one support and the other end on the other support.

For the purpose of mounting the spring in a reproducible manner, it is also important that the spring will always assume the same position in its longitudinal direction when the torque is zero. For this reason, one support for each spring is horizontally displaceable and can be fixed in an adjusted position. The correct position of the displaceable support is determined on the electrical display. If the support is displaced, the display is influenced. The displaceable support may be a carriage displaceable on a platform by an adjusting screw and securable in position by a set screw at right-angles to the adjusting screw. Alternatively, it is possible to have a stationary support and to stress the spring to a greater or smaller extent by displacing one of the sleeve or clip-like terminals.

Another way of mounting the motor involves the provision of a housing on the hollow shaft, either placed thereon or made in one piece therewith, the motor being accommodated in the housing. The housing has an aperture in which the exchangeable gears are disposed. This makes them easily accessible from the outside.

More particularly, the motor comprises a downwardly directed output shaft aligned with the measuring shaft and a laterally offset intermediate shaft is coupled to the output shaft and measuring shaft, the exchangeable pair of gears being disposed between the output shaft and intermediate shaft or intermediate shaft and measuring shaft.

Two examples of the invention will now be described in more detail with reference to the accompanying drawings, wherein.

Figure 1:
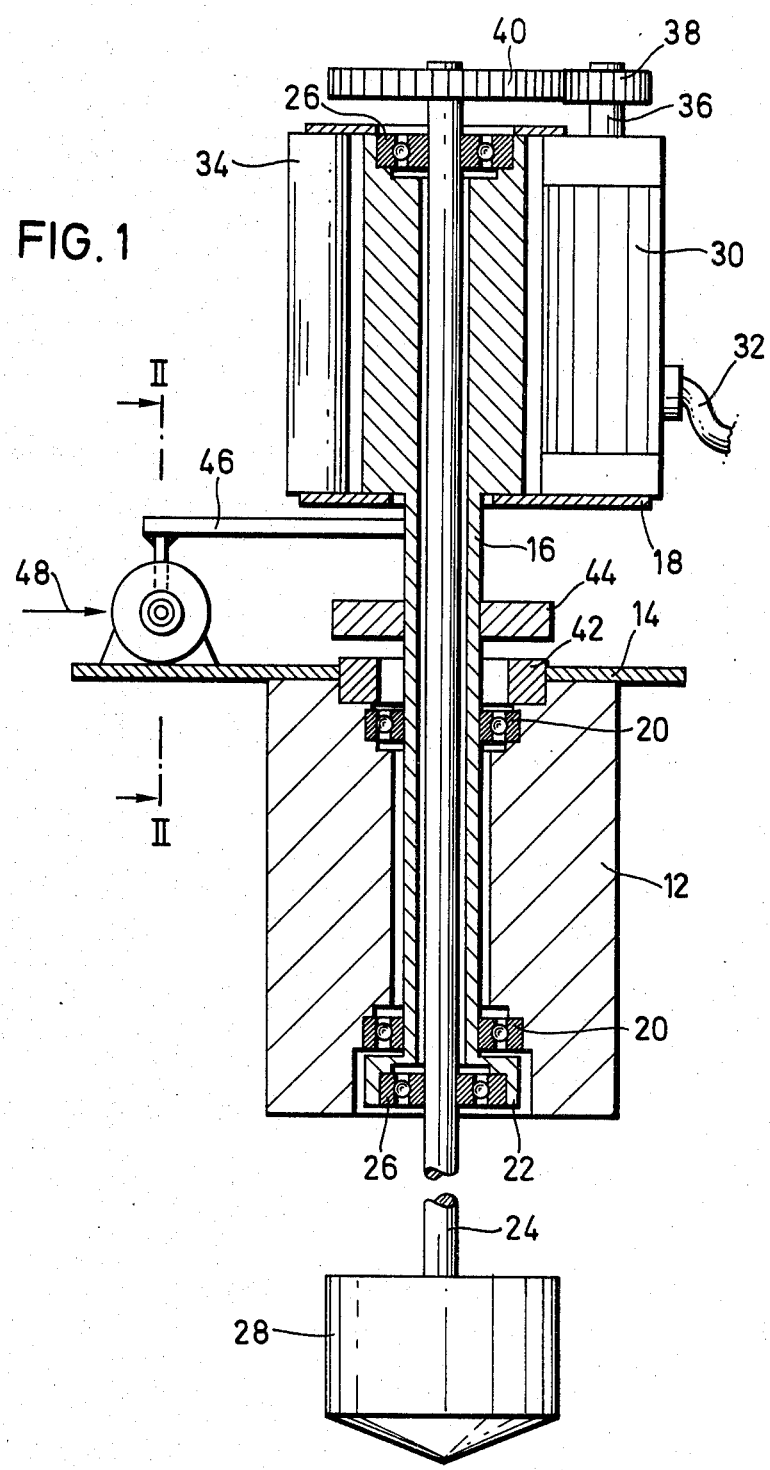
FIG. 1 is a part-sectional side elevation of a fist embodiment of rotary viscometer.

FIG. 1 shows the base block 12 on which the base plate 14 is secured, and the hollow shaft 16 passing through the base block. A plate constituting the support 18 for the drive motor is secured to the hollow shaft 16. The hollow shaft 16 is mounted in the base block 12 by two bearings 20. At its lower end, the hollow shaft 16 has a section 22 of enlarged diameter. The measuring shaft 24 is concentrically disposed within the hollow shaft 16. It is mounted in two bearings 26. Those bearings 26 are in turn seated in the hollow shaft 16. It will be seen that the bearings 20 for the hollow shaft 16 and the bearings 26 for the measuring shaft 24 have practically the same diameter or exactly the same diameter. The measuring member 28 is seated at the lower end of the measuring shaft 24. It is immersed in the substance to be measured. The drive motor 30, of which the speed is regulatable, is seated on the support 18. Electric energy is supplied to the motor through leads 32. A counterweight 34 is positioned on the other side of the support 18. The drive motor 30 has an output shaft 36. A gear 38 is seated thereon. It meshes with a gear 40 on the measuring shaft 24. A permanent magnet 42 is provided on the base block 12 and partially sunk therein. A second permanent magnet 44 at a small spacing therefrom is secured to the hollow shaft 16. The lower permanent magnet 42 has a larger internal and a smaller external diameter than the upper permanent magnet 44. The shaft 16 also has an arm 46 secured to it. It leads to the inductive transducer 48. The latter as well as the other components for measuring the torque will now be described with reference to FIG. 2.

Figure 2:
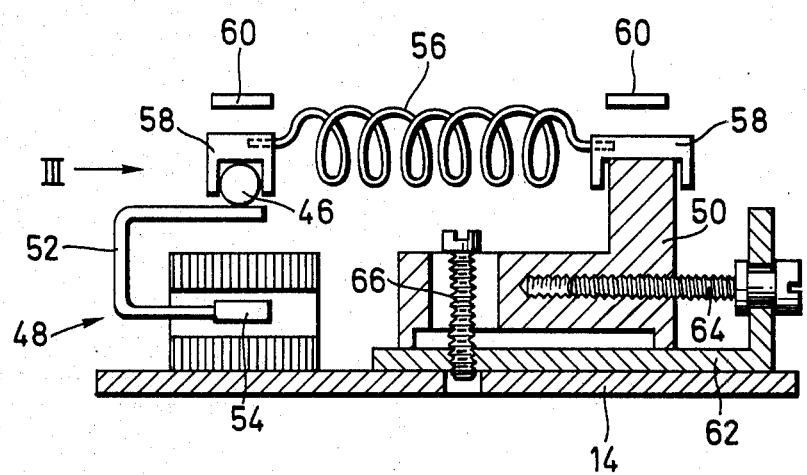
FIG. 2 is a section on the line II—II in FIG. 1 showing the transducer and spring and the spring mounting.

FIG. 2 shows the displaceable support 50 for one end or terminal of an exchangeable spring 56. The other terminal of the spring is placed on the arm 46 which is connected to a bracket 52. The bracket 52 carries a core 54. This core is disposed within the inductive transducer 48 or rather within the coil thereof. The two clip-like terminals 58 are secured to the spring 56. It will be evident that the terminal 58 placed on the arm 46 is narrower than the terminal 58 placed on the support 50. Two clamping plates 60 lie on the terminals 58 from above. They may be biassed by springs (not shown). The support 50 is displaceable on the platform 62. An adjusting screw 64 is provided to bring about the displacement. The adjusted position is fixed with the aid of the set screw 66.

Figure 3:
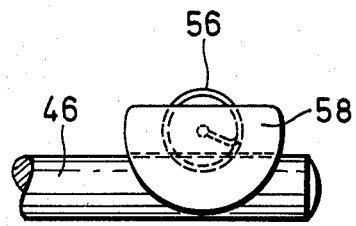
FIG. 3 is an elevation taken in the direction of the arrow III in FIG. 2 showing the clip-like terminal of a spring and its support.

FIG. 3 shows the arm 46 from the side and the front of the spring 56 and its clip-like terminal 58 placed on the arm.

Figure 4:
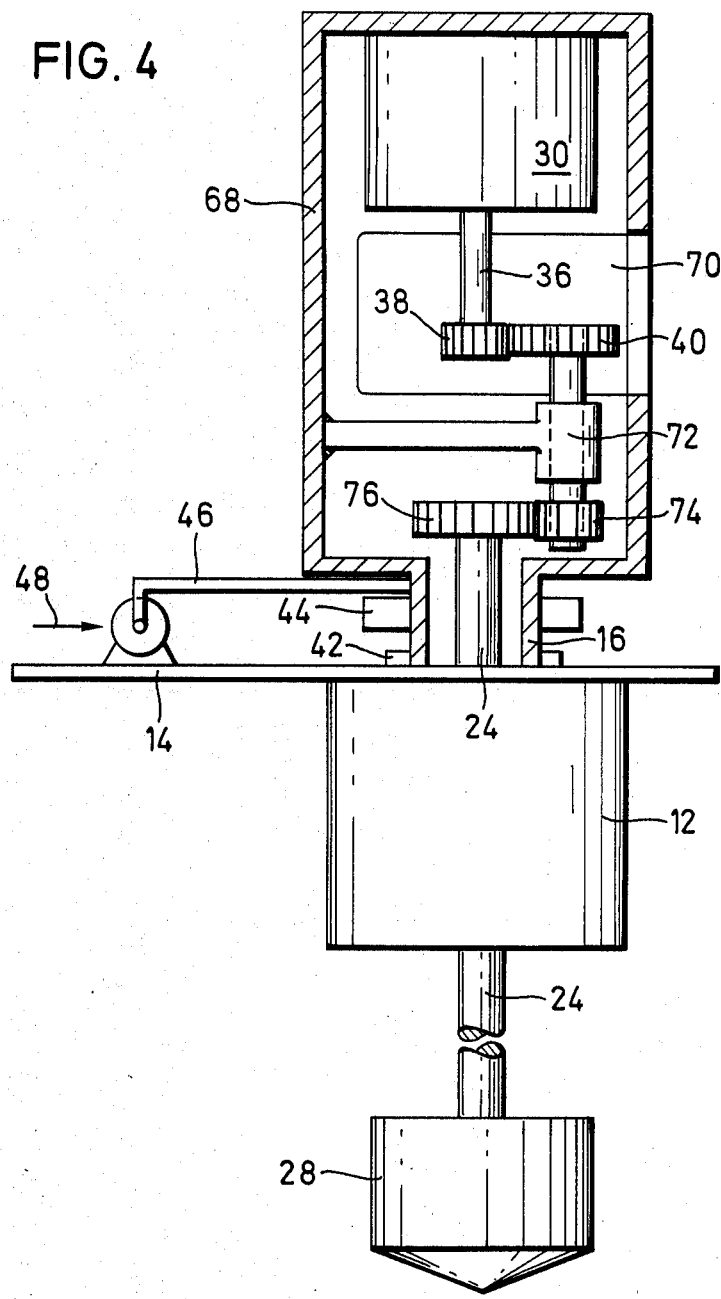
FIG. 4 is a part-sectional side elevation of a second embodiment of rotary viscometer.

Referring to FIG. 4, a second embodiment of rotary viscometer has a different arrangement for the motor 30 and the following description will refer only to this different arrangement of motor. The hollow shaft 16 is enlarged to define a housing 68 in which the motor 30 is centrally disposed. At the side, the housing 68 is provided with an aperture 70. The exchangeable gears 38 and 40 are located in this aperture 70 or in line therewith. The gear 38 is seated on the output shaft 36 of motor 30. The gear 40 is seated on an intermediate shaft 72. The intermediate shaft also carries a further gear 74 which engages with a gear 76 on the measuring shaft 24.

To use the rotary viscometer, gears 38 and 40 of the desired number of teeth to provide the desired transmission ratio are placed on the output shaft 36 and measuring shaft 24. Adjustment of the rotary speed may be effected by an automatic control of the motor 30. The motor speed is then regulated by the set-point adjustment. A spring 56 having the required characteristic is also inserted to suit the rotary speed and the viscosity of the substance to be measured. The correct position of the spring is determined by the shape, size etc. of the clip-like terminals 58. The zero position of the spring 56 is set by means of the adjusting screw 64 and is fixed by the set screw 66. To give an indication of numerical values, it may be mentioned that a motor covers a speed range of, say, 1:1000 and this range can be increased by a factor of, for example, up to 25 by exchanging the gears 38 and 40. With a spring 56 and an inductive transducer 48 of which the measuring range can be switched over electrically, it is possible to cover a range of, e.g., 1:100. By using a different spring, this torque range can for example be increased 20 times.

In operation, the measuring member 28 revolves in the substance to be examined. By reason of the counter-torque that is thereby created, the motor 30 is turned about the axis of the hollow shaft 16. This rotation is transmitted to the arm 46. The spring 56 is thereby stressed and opposes this movement. The motion of the arm 46 is transmitted to the bracket 52 and results in displacement of the core 54 in the inductive transducer 48. The latter indicates a displacement of the core 54. The scale may be graduated directly in the units that are required. During operation, and on turning of the measuring shaft 24, friction in the bearings 26 mounting the measuring shaft is not introduced in the measurement. The bearings 26 belong to the internal system of the arrangement. Consequently, the bearings 26 could be simple slide bearings. On the other hand, the friction of the bearings 20 for the hollow shaft 16 is introduced in the measurement as blind friction. The blind friction determines the smallest measurable torque resulting from the viscosity. Altogether, the hollow shaft 16 only turns through a maximum of about 3°. Since the bearings 20 of the hollow shaft 16 have only a small internal and external diameter, the amount of blind friction influencing the measurement is very small indeed.

The foregoing description shows that the gears 38 and 40 for altering the rotary speed range and the spring 56 for altering the torque measurement range can be readily exchanged. They are easily accessible from the outside. The description also shows that the counter-torque swings the motor 30 about the axis of the hollow shaft 16 practically without friction. The bearings 20 for mounting the hollow shaft 16 has a small external diameter. By means of the permanent magnets 42 and 44, they are relieved of axial forces. For this purpose, the strength of the permanent magnets is tuned to the weight of the hollow shaft 16, support 18, motor 30 etc. By means of the counterweight 34, torques about the vertical are excluded. This also serves to relieve the bearings.

I claim:

1. A rotary viscometer comprising a variable speed electric drive motor having a rotor and a stator, said variable speed drive motor also including a speed indicator such as a tachogenerator or a similar device, a measuring shaft driven by said motor, a measuring member at one end of said measuring shaft for immersion in a medium to be measured, said motor stator being rotatably mounted on a base block by means of a support and subjected to the return force of a spring, the rotary deflection of said stator from a rest position being measurable over a short path, characterized in that the force path between said motor and measuring shaft includes at least one pair of exchangeable gears or toothed belts, and one of a plurality of springs having different characteristics is selectively insertable between said motor support and said base block and further characterized in that said support is part of a hollow shaft and the measuring shaft extends through and is mounted in said hollow shaft.

2. The viscometer of claim 1, wherein the axes of said motor and hollow shaft are parallel.

3. The viscometer of claim 1, wherein said hollow shaft passes through said base block and is mounted therein, and said motor and spring are disposed above said base block.

4. The viscometer of claim 1, wherein an output shaft of said motor is disposed at the top and said pair of gears or toothed belts is disposed between said output shaft and the parallel upper end of said measuring shaft.

5. The viscometer of claim 3, including annular permanent magnets which repel each other coaxially disposed on said base block and hollow shaft coaxial with said hollow shaft.

6. The viscometer of claim 5, wherein one of said permanent magnets has a smaller external diameter and larger internal diameter than the other of said permanent magnets.

7. The viscometer of claim 3, wherein the part of said hollow shaft disposed within said base block comprises at least one section of enlarged diameter and a first bearing for said measuring shaft is inserted in said section, second bearings for mounting said hollow shaft in said base block having the same external diameter as said first bearing.

8. The viscometer of claim 1, wherein said springs are helical and carry sleeve or clip-like terminals.

9. The viscometer of claim 8, wherein said terminals and supports therefor are constructed so that said springs are insertable in only one defined position.

10. The viscometer of claim 9, wherein one support for each spring is horizontally displaceable and can be fixed in an adjusted position.

11. The viscometer of claim 10, wherein said one support is displaceable on a platform by an adjusting screw and can be fixed in position by a set screw at right-angles to said adjusting screw.

12. The viscometer of claim 1, wherein a housing on said hollow shaft accommodates said motor.

13. The viscometer of claim 12, wherein said housing comprises an aperture in which said exchangeable gears are disposed.

14. The viscometer of claim 12, wherein said motor comprises a downwardly directed output shaft aligned with said measuring shaft and a laterally offset intermediate shaft is coupled to said output shaft and measuring shaft, said exchangeable pair of gears being disposed between said output shaft and intermediate shaft or said intermediate shaft and measuring shaft.

* * * * *